US012721885B2

(12) United States Patent
Jacobs et al.

(10) Patent No.: US 12,721,885 B2
(45) **Date of Patent: *Sep. 1, 2026**

(54) **VACCINE AGAINST *HEAMOPHILUS PARASUIS***

(71) Applicant: Intervet Inc., Madison, NJ (US)

(72) Inventors: Antonius Arnoldus Christiaan Jacobs, Kessel (NL); Theodora Johanna Van Kasteren-Westerneng, Arnhem (NL); Johanna Jacoba Elisabeth Bijlsma, Nijmegen (NL)

(73) Assignee: Intervet Inc., Rahway, NJ (US)

( * ) Notice: Subject to any disclaimer, the term of this patent is extended or adjusted under 35 U.S.C. 154(b) by 902 days.

This patent is subject to a terminal disclaimer.

(21) Appl. No.: 17/775,411

(22) PCT Filed: Nov. 19, 2020

(86) PCT No.: PCT/EP2020/082640

§ 371 (c)(1), (2) Date: May 9, 2022

(87) PCT Pub. No.: WO2021/099446

PCT Pub. Date: May 27, 2021

(65) Prior Publication Data

US 2022/0387577 A1 Dec. 8, 2022

(30) Foreign Application Priority Data

Nov. 20, 2019 (EP) .................................... 19210259

(51) Int. Cl.
*A61K 39/102* (2006.01)
*A61P 31/04* (2006.01)

(52) U.S. Cl.
CPC ............ *A61K 39/102* (2013.01); *A61P 31/04* (2018.01)

(58) Field of Classification Search
CPC .............................. A61K 39/102; A61P 31/04
See application file for complete search history.

(56) References Cited

U.S. PATENT DOCUMENTS

2022/0378899 A1* 12/2022 Jacobs .................... A61P 31/04
2022/0378900 A1* 12/2022 Jacobs .................... A61P 31/04

FOREIGN PATENT DOCUMENTS

WO 2015181356 A1 12/2015

OTHER PUBLICATIONS

GeneBank page for No. 32961. (https://www.ncbi.nlm.nih.gov/protein/ACL32961.1?report=genpept). Earliest submission Dec. 2008. (Year: 2008).*

GeneBankpageforNo. 32961.(https:/Avwww.ncbi.nim.nih.gov/protein/ACL32961.1?report=genpept).Earliest submission Dec. 2008. (Year: 2008).*

Zhangetal.Immunologicalidentificationandcharacterizationofextracellularserineprotease-likeproteinencodedinaputativeespP2geneofHaemophilusparasuis.JVetMedSci.Aug. 2012;74(8):983-7.doi:10.1292/jvms.11-0260.EpubMar. 26, 2012.PMID:22446405 (Year: 2012).*

Anonymous: "autotransporter outer membrane beta-barrel domain-containing protein [—Protein—NCBI", Jul. 28, 2019 (Jul. 28, 2019), XP055692374, Retrieved from the Internet: URL:https://www.ncbi.nlm.nih.gov/protein/W P 040978900 [retrieved on May 6, 2020] * the whole document * , 2 pages.

Anonymous: "putative extracellular serine protease (autotransporter) [Glaesserella—Protein—NCBI", Jan. 30, 2014 (Jan. 30, 2014), XP055692655, Retrieved from the Internet: URL:https://www.ncbi.nlm.nih.gov/protein/A CL32961.1 [retrieved on May 7, 2020] * the whole document * , 2 pages.

Barasuol, Bibiana Martins et al., New insights about functional and cross-reactive properties of antibodies generated against recombinant TbpBs of Haemophilus parasuis, Scientific Reports, 2017, 1-13, 7(1).

Frandoloso, Rafael et al., Development and Characterization of Protective Haemophilus parasuis Subunit Vaccines Based on Native Proteins with Affinity to Porcine Transferrin and Comparison with Other Subunit and Commercial Vaccines, Clinical and Diagnostic Laboratory Immunology, 2011, 50-58, 18(1).

Li Miao et al., Development and antigenic characterization of three recombinant proteins with potential for Glässer's disease prevention, Vaccine, 2016, 2251-2258, 34(19).

Li, Miao et al., Evaluation of immunogenicity and protective efficacy of recombinant outer membrane proteins of Haemophilus parasuis serovar 5 in a murine model, PLOS One, 2017, 1-15, 12(4): e0176537.

Li, Miao et al., Identification of secreted proteins as novel antigenic vaccine candidates of Haemophilus parasuis serovar 5, Vaccine, 2015, 1695-1701, 33(14).

Lucchese, G et al, How a single amino acid change may alter the immunological information of a peptide, Frontiers in Bioscience: Elite Edition, 2012, 1843-1852, vol. 4, No. 5.

McCaig, William D.et al., Characterization and Vaccine Potential of Outer Membrane Vesicles Produced by Haemophilus parasuis, PLOS One, 2016, 1-23, 11(3): e0149132.

Olvera, Alex et al., Virulence-associated trimeric autotransporters of Haemophilus parasuis are antigenic proteins expressed in vivo, Veterinary Research, 2009, 1-11, 41(3).

* cited by examiner

*Primary Examiner* — Misook Yu
*Assistant Examiner* — Alec Jon Peters
(74) *Attorney, Agent, or Firm* — Susanna C. Benn

(57) ABSTRACT

The invention pertains to a serine protease antigen which induces antibodies against a protein having at least 69% sequence identity with the *Haemophilus parasuis* protein according to SEQ ID No: 1, for use in a prophylactic method to protect a pig against an infection with *Haemophilus parasuis* by administering a vaccine to the pig, wherein the vaccine comprises the serine protease antigen. The invention also pertains to a vaccine, a method to manufacture such a vaccine and a method to protect a pig against *H. parasuis*.

7 Claims, No Drawings

Specification includes a Sequence Listing.

VACCINE AGAINST *HEAMOPHILUS PARASUIS*

CROSS-REFERENCE TO RELATED APPLICATIONS

This application is a National Stage application of International Patent Application No. PCT/EP2020/082640, filed Nov. 19, 2020, which claims priority to European Patent Application No. EP 19210259.8, filed Nov. 20, 2019.

GENERAL FIELD OF THE INVENTION

The invention in general pertains to the treatment of pigs against an infection with the pathogenic bacterium *Haemophilus parasuis*. In particular the invention pertains to a novel vaccine for prophylactically treating pigs against an infection with this bacterium.

BACKGROUND OF THE INVENTION

*Haemophilus parasuis* is one of the most important bacteria affecting pigs. The disease caused by this pathogen is characterized by polyserositis and it is known as Glässer's disease. *Haemophilus parasuis* is present in all major swine-rearing countries and remains a significant pathogen in contemporary swine production systems. In addition to causing disease, *Haemophilus parasuis* is frequently isolated from the upper respiratory tract of healthy pigs. There are different serotypes known of *Haemophilus parasuis*, each of these can be identified using the technique of immunodiffusion (Kielstein et al. in J. Clin. Microbiol. 30:862-865; 1992 and Rapp-Gabrielson et al. in AJVR 53:659-664; 1992). Successful vaccination resulting in decreased mortality has been achieved by various types of vaccines.

Inactivated *H. parasuis* (i.e. bacterin) vaccines are widely used today. All commercially available *H. parasuis* vaccines are inactivated vaccines. Most of the currently available commercial vaccines are produced by propagating a virulent *H. parasuis* strain where after the strain is inactivated. Bacterial cultures are pelleted by high-speed centrifugation and resuspended in sterile phosphate buffer saline, and subsequently formulated with an appropriate adjuvant such as mineral oil, aluminum hydroxide, Carbopol, saponin, vitamin E acetate, squalene, squalene etc. In addition to monovalent vaccines, there are bivalent, trivalent, or tetravalent *H. parasuis* vaccines, which include various serotypes. They generally provide a low level of cross-protection, and they are more efficacious against homologous serotypes. These inactivated vaccines, such as for example Porcilis Glässer (MSD, Boxmeer, The Netherlands) play important roles in controlling Glässer's disease outbreaks throughout the world.

Stably attenuated *H. parasuis* strains could in theory serve as safe and efficacious vaccines. However, the development of attenuated *H. parasuis* vaccines has been limited because of the lack of knowledge regarding the major virulence factors of *H. parasuis*, which makes it difficult to create *H. parasuis* mutants that could serve as potential vaccines. To date, there are no genetically engineered, live attenuated or inactivated *H. parasuis* vaccine candidates.

Several subunit vaccines have been studied, but existing data suggest that a few subunit vaccines induce high levels of anti-*H. parasuis* neutralizing antibodies and protect pigs against *H. parasuis* challenge. However, commercial subunit vaccines that prevent and control Glässer's disease are not available currently. Recently (Huisheng Liu et al, in *Veterinary Immunology and Immunopathology*, Volume 180, 1 Nov. 2016, pp 53-58), subunit vaccines that comprise newly identified protective antigens such as recombinant transferrin-binding protein B (TbpB), outer membrane protein (OMP) formulations enriched with TbpB, OMP2 and OMP5, transferrin-binding protein A (TbpA), trimeric autotransporters (VtaA), six secreted proteins (PflA, Gcp, Ndk, HsdS, RnfC, and HAPS_0017), three glyceraldehyde-3-phosphate dehydrogenase (GAPDH), OapA, and HPS-0675 fusion proteins, various alternative OMPs (SmpA, YgiW, and FOG), 6-phosphogluconate-dehydrogenase, cytolethal distending toxin subunits A, B, and C, and neuraminidase or lipoprotein, have been proven to provide partial protection against *H. parasuis* challenge.

To date, also a DNA vaccine has been shown to be able and provide some partial protection against *H. parasuis*. The vaccine comprises DNA encoding *H. parasuis* GAPDH.

However despite the commercial availability of vaccines, antimicrobials still are widely used to treat *H. parasuis* infections mainly due to incomplete efficacy of many existing vaccines. Pigs receiving antimicrobials early during infection with *H. parasuis* are usually able to survive a systemic infection. However, there is a lot of pressure to reduce the amount of antimicrobials used for growing pigs.

OBJECT OF THE INVENTION

It is an object to provide an alternative vaccine to prophylactically treat a pig against an infection with *H. parasuis*, which vaccine preferably provides protection at least as good as a conventional bacterin vaccine.

SUMMARY OF THE INVENTION

In order to meet the object of the invention, it was found that a serine protease antigen which induces antibodies against a protein having at least 69% sequence identity with the *Heamophilus parasuis* protein according to SEQ ID No: 1, can be used in a prophylactic method to protect a pig against an infection with *Haemophilus parasuis* by administering a vaccine to the pig, wherein the vaccine comprises the serine protease antigen.

The fact that this serine protease antigen can be used in order to treat a pig against an infection with *H. parasuis* was based on the surprising finding that the native protein, a putative serine protease which is conserved in various *H. parasuis* serotypes (including the virulent serotypes 4, 5, 12, 13 and 15), plays a key role in the infection with *H. parasuis*. This could be established since vaccinating with (part of) the naturally occurring protein led to a very good protection against pathogenic *H. parasuis*, at a level that is even better than protection that can be arrived at a conventional and well established bacterin vaccine. This shows that this serine protease plays a key role in the pathogenicity of the bacterium, and that neutralizing the function of this protein helps in decreasing the infection, including the clinical disease resulting therefrom. In that respect, the merit of the inventors lies in the recognition that this serine protease plays a key role in the pathogenicity of *H. parasuis*. Once this was recognized, it followed that inducing antibodies against this protein would be effective as a treatment against an infection with *H. parasuis*.

With respect to the protein according to SEQ ID No: 1, across various serotypes, the natural variation of the protein over its full length is about 69%. So using a serine protease antigen that induces antibodies against the native protein that meets this identity level, can be used to arrive at protection against the various wild type *H. parasuis* strains of different serotypes that naturally produce the corresponding protein.

A straightforward way of inducing such antibodies is to administer the wild type protein as such. Indeed, for finding the gist of the invention the protein having the amino acid sequence according to the (complete) SEQ ID No:1 was used as antigen to induce antibodies against the natural protein. However, it is commonly known that when antibodies need to be raised against a certain (naturally occurring) protein, it is typically not necessary to use the whole protein. Also, small variations of the natural protein (typically at least up to 30%), may still be useful as effective antigen and capable of inducing neutralizing antibodies.

With respect to the former, it is commonly known that it is possible to use a so called immunogenic fragment of that protein that is capable, as such or coupled to a carrier such as e.g. KLH, of inducing an immune response against the corresponding protein. This is in particular true for the serine protease as identified in the present invention. To start with, the protein according to SEQ ID No:1 is already only a part of the naturally occurring protein, which includes an autotransporter beta barrel. Next to this, although its function in the pathogenicity of *H. parasuis* remains unknown, it was found that the protein is homologous to the human Mac-1 protein. This could be established via a so called Cobalt alignment: a multiple sequence alignment tool that finds a collection of pairwise constraints derived from conserved domain database, protein motif database, and sequence similarity, using RPS-BLAST, BLASTP, and PHI-BLAST, wherein pairwise constraints are then incorporated into a progressive multiple alignment (see Papadopoulos J S and Agarwala R, Bioinformatics 23:1073-79, 2007; PMID: 17332019). This was confirmed by a search in the NCBI database for "Mac-1 family" protein in "*Haemophilus*" bacteria, which confirmed the presence of a protein with a Mac-1 domain homologue in *H. parasuis*. The Mac-1 protein on its turn is known to be homologous to an IgM protease of the pig pathogenic bacterium *Streptococus suis* as described in WO 2015/181356 (IDT Biologika GmbH). As taught in WO 2015/181356, a vaccine directed against the full length protein or a fragment comprising only the highly conserved Mac-1 domain, is able to induce antibodies against the full length naturally occurring protein, therewith providing protection against the corresponding bacterium. Although *H. parasuis* is totally unrelated to *S. suis*, the fact that both bacteria produce a protein with a Mac-1 domain homologue, which is known to have immunoglobulin peptidase activity (see PFAM database of the European Molecular Biology Institute, as confirmed in WO 2015/181356), combined with the fact that the diseases are clinically alike (they both lead to polyserositis, typically are pathogenic only for piglets, and are both induced by stress such as weaning and transport), indicates that also in *H. parasuis*, like in *Streptococcus suis*, the corresponding natural protein is involved in immune evasion. Moreover, the fact that in both pathogenic bacteria the Mac-1 domain is highly conserved across serotypes, but that for the remainder the *H. parasuis* and *Streptococcus suis* proteins are completely unrelated (identity level over the whole protein, including the Mac-1 domain, is as low as 13%), combined with the fact that across *H. parasuis* serotypes 3, 4, 5, 9, 12, 13 and 15 the identity of the Mac-1 domain is even 100% (whereas for the remainder of the protein this is much lower, down to 69%), even evidence that the Mac-1 domain contains the prime immunogenic epitope(s), and thus on itself is able to induce antibodies that neutralize the naturally occurring serine protease that comprises this so-called Mac-1 domain. Preferably the fragment comprises the naturally occurring Mac-1 domain of *H. parasuis*, i.e. the sequence according to SEQ ID NO:2.

However, as is commonly known, addressing the second issue as identified here above, small variations of 10-20%, even up to 30% in sequence identity, of a particular naturally occurring polypeptide may still be useful as effective antigen and capable of inducing neutralizing antibodies. These variations can be reflected by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science 227, 1435-1441, 1985) and determining the functional similarity between homologous proteins. Such amino acid substitutions of the exemplary embodiments of this invention, as well as variations having deletions and/or insertions are within the scope of the invention. Therefore, the serine protease antigen for use in the present invention could for example be a polypeptide that is at least 70% identical to the polypeptide according to SEQ ID NO:2, preferably at least 75, 80, 85, 90, 91, 92, 93, 94, 95, 96, 97, 98, 99% or higher.

Next to the protein or fragments thereof for use as an antigen to induce antibodies against the naturally occurring serine protease, it is known that nucleic acids (DNA, RNA etc) can be used as antigen to induce antibodies against the corresponding protein. Although the immune system does not act directly against the nucleic acids themselves, but against the proteins encoded by them, and thus technically it is not 100% correct to identify these nucleic acids as "antigen", it is accepted to refer to such nucleic acids or a vector comprising such nucleic acids for the same purpose as antigen. In the present invention, such nucleic acids or a vector comprising such nucleic acids are also identified as "antigen". Commonly used vectors are viral vectors such as Adenovirus and Herpes virus of turkeys.

A variation on the use of viral vector vaccines is the use of vaccines of replicon particles (RP; see Lundstrom, 2014, Vaccines, vol. 6, p. 2392-2415). These are virus-like particles but comprise a defective viral genome and typically, a heterologous gene.

These replicon particles comprise RNA packaged in particles (i.e., they are encapsidated) such that they are able to enter a target animal host cell and perform one round of viral genome amplification without the ability to form new particles. The replicon particle does not propagate from the infected cell, as it lacks the necessary structural protein-coding sequence(s). As such, they are more similar to wild-type virus than other replicon vaccines such as naked RNA vaccines, or vaccines comprising RNA launched from a DNA plasmid (Hikke, 2017, Anu. Rev. Anim. Biosci. 2017, 5; 10.1-10.21). The genome of the RP's typically express a heterologous gene encoding an immunoprotective antigen. Multiple RNA viruses have been used in the production of RP's, such as members of the positive stranded Flaviviridae, Picornaviridae and Arteriviridae, or negative stranded RNA viruses such as Bunyavirus, Paramyxovirus and Rhabdovirus. Most widely used and most extensively studied are Alphavirus RNA replicon particles (Vander Veen et al., 2012, Anim. Health. Res. Rev., vol. 13, p. 1-9; and: Kamrud et al., 2010, J. Gen. Virol., vol. 91, p. 1723-1727), which are therefore preferred for practical reasons. Also, Alphavirus RP's are believed to be somewhat stronger immunopotentiators than other RP's known in the art and based on other viruses such as the bunyavirus. Several Alphavirus species have been used to develop RP vaccines, e.g.: Venezuelan equine encephalitis virus (VEEV) (Pushko et al., 1997, Virology, vol. 239, p. 389-401), Sindbis virus (Bredenbeek et al., 1993, J. of Virol., vol. 67, p. 6439-6446), and Semliki Forest virus (Liljestrom & Garoff, 1991, Biotechnology (NY), vol. 9, p. 1356-1361). RP vaccines (VEE based) are the basis of several USDA-licensed vaccines, which include: Porcine Epidemic Diarrhea Vaccine, RNA (Product Code 19U5.P1), Swine Influenza Vaccine, RNA (Product Code 19A5.D0), Avian Influenza Vaccine, RNA (Product Code 19O5.D0), and Prescription Product, RNA Particle (Product Code 9PP0.00).

All in all, it was found that using a serine protease antigen according to the invention, in particular an *Haemophilus parasuis* serine protease antigen (i.e. an antigen corresponding to the serine protease as expressed by *Haemophilus parasuis*, i.e. the naturally occurring protein as such or a protein having at least 69% sequence identity therewith, or an immunogenic fragment thereof, or a nucleic acid encoding for such a protein or a fragment thereof), in a vaccine, one is able to induce antibodies that are directed against the naturally occurring *H. parasuis* serine protease. Since it is recognized that this serine protease plays a key role in immune evasion of the wild type bacterium, this means that by raising antibodies against this protein, one is able to treat a (post-vaccination) infection with *H. parasuis* by effectively acting against its immune evasion system. For example, based on homology with the human Mac-1 protein and *Streptococcus suis* which produces an IgM protease comprising a Mac-1 domain, it is understood that a polypeptide comprising the Mac-1 domain of the current serine protease (optionally coupled to an immunogenic carrier such as for example KLH) is sufficient, when used as antigen in a vaccine, to induce antibodies against the naturally occurring protein. The same is true for an RP vaccine comprising RNA encoding this Mac-1 domain.

The invention is also embodied in a vaccine to protect a pig against an infection with *Haemophilus parasuis*, the vaccine comprising a serine protease antigen which induces antibodies against a protein having at least 69% sequence identity with the *Heamophilus parasuis* protein according to SEQ ID No: 1, and a pharmaceutically acceptable carrier.

The invention also pertains to the use of a serine protease antigen which induces antibodies against a protein having at least 69% sequence identity with the *Heamophilus parasuis* protein according to SEQ ID No: 1, for manufacturing a vaccine for protecting a pig against an infection with *Haemophilus parasuis*.

Next to this, the invention also pertains to a method to protect a pig against an infection with *Haemophilus parasuis* by administering a vaccine to the pig, the vaccine comprising a serine protease antigen which induces antibodies against a protein having at least 69% sequence identity with the *Heamophilus parasuis* protein according to SEQ ID No: 1.

Definitions

An antigen is antigenic material derived from a microorganism, notwithstanding that the antigen is ultimately artificially produced. An antigen initiates and mediates the formation of an antibody that acts against the corresponding naturally occurring compound (typically a protein). Bacteria, viruses, protozoans, and other microorganisms are important sources of antigens. These may for example correspond to proteins or polysaccharides derived from the outer surfaces of the cell (capsular antigens), from the cell interior (the somatic or O antigens), from the flagella (the flagellar or H antigens), or from excreted products including for example enzymes and toxins.

A vaccine is a constitution suitable for application to an animal, comprising one or more antigens in an immunologically effective amount, i.e. capable of stimulating the immune system of the target animal sufficiently to induce an immune response, such as antibodies, against the corresponding naturally occurring proteins, typically combined with a pharmaceutically acceptable carrier (i.e. a biocompatible medium, viz. a medium that after administration does not induce significant adverse reactions in the subject animal, capable of presenting the antigen to the immune system of the host animal after administration of the vaccine) such as a liquid containing water and/or any other biocompatible solvent or a solid carrier such as commonly used to obtain freeze-dried vaccines (based on sugars and/or proteins), optionally comprising immunostimulating agents (adjuvants), which upon administration to the animal induces an immune response that is able to protect the animals against a (post-vaccinating) infection.

A prophylactic method is a method designed to protect against an infection or the corresponding disease by acting before the infection actually occurs, typically by treating a subject animal with a vaccine before the subject animal is expected to become infected.

To protect a pig against an infection with *H. parasuis* means aiding in preventing, ameliorating or curing a pathogenic infection with *H. parasuis*, or aiding in preventing, ameliorating or curing a disorder arising from that infection, for example to prevent or reduce one or more clinical signs resulting from the infection with *H. parasuis*.

An immunogenic fragment is a fragment of a protein that still has retained its capability to induce an immune response in a host, i.e. comprises a B- or T-cell epitope. A variety of techniques is commonly available to easily identify immunogenic fragments (determinants), in particular immunogenic fragments of proteins. The method described by Geysen et al (Patent Application WO 84/03564, Patent Application WO 86/06487, U.S. Pat. No. 4,833,092, Proc. Natl Acad. Sci. 81:3998-4002 (1984), J. Imm. Meth. 102, 259-274 (1987), the so-called PEPSCAN method is an easy to perform, quick and well-established method for the detection of immunogenic epitopes of proteins. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47:45-148 (1987) and U.S. Pat.

No. 4,554,101). T-cell epitopes can likewise be predicted from the sequence by computer with the aid of Berzofsky's amphiphilicity criterion (Science 235, 1059-1062 (1987) and U.S. patent application Ser. No. 07/005,885). A condensed overview is found in: Shan Lu on common principles: Tibtech 9:238-242 (1991), Good et al on Malaria epitopes; Science 235:1059-1062 (1987), Lu for a review; Vaccine 10:3-7 (1992), Berzofsky for HIV-epitopes; The FASEB Journal 5:2412-2418 (1991). It is common general knowledge that peptides in order to be immunogenic need to be of a minimal length; 8-11 aa for MHC I receptor binding, and 11-15 aa for MHC II receptor binding (reviewed e.g. by R. N. Germain & D. H. Margulies, 1993, Annu. Rev. Immunol., vol. 11, p. 403-450: The biochemistry and cell biology of antigen processing and presentation).

Sequence identity between two polypeptides (or nucleic acids) means the percentage of identical amino acids (or nucleotides) in overlapping regions of the polypeptides (or nucleic acids) as established with the BLAST program using the blastp algorithm with default parameters (see Tatiana A. Tatusova, Thomas L. Madden FEMS Microbiol. Letters 174:247-250; 1999).

FURTHER EMBODIMENTS OF THE INVENTION

In a further embodiment, the serine protease antigen induces antibodies against a protein having at least 90% sequence identity with the protein according to SEQ ID No: 1, preferably against a protein having at least 95% sequence identity with the protein according to SEQ ID No: 1, for example a protein being identical to SEQ ID No: 1.

In another embodiment the serine protease antigen comprises or encodes (the latter when the antigen is or comprises the corresponding nucleic acid) a polypeptide having at least 70% identity with the Mac-1 domain according to SEQ ID No:2 of the said *Haemophilus parasuis* protein, preferably at least 80%, 90% or even 100% identity with the Mac-1 domain according to SEQ ID No:2 of the said *Haemophilus parasuis* protein.

In yet another embodiment the serine protease antigen is or encodes a protein having at least 69% sequence identity with the *Haemophilus parasuis* protein according to SEQ ID No: 1.

In another embodiment the serine protease antigen is for use in a method to protect the pig against an increased risk of mortality due to the infection with *Haemophilus parasuis*.

In yet another embodiment the serine protease antigen is for use in a method to protect the pig against one or more clinical signs due to the infection with *Haemophilus parasuis*.

The invention will now be further illustrated using the following specific examples.

EXAMPLES

Example 1

Objective

The objective of this alignment experiment was to find the sequence identity level of the serine protease across various *H. parasuis* strains of various serotypes, and to identify the Mac-1 domain in the serine protease.

Results

In the table here below, it is indicated what the sequence identity is with respect to SEQ ID No:1 for the corresponding serine proteases in other *H. parasuis* strains. It appears that the level of identity is at least 69% among various strains of common serotypes. For strains within the group of known highly pathogenic and most prevalent serotypes 4, 5, 12 and 13, the level of identity is even 90% or higher.

TABLE 1

Sequence identity with SEQ ID No: 1 for various *H. parasuis* strains

| Strain | Start | End | % Identity |
|---|---|---|---|
| Serotype 3 - strain SW1 | 1 | 491 | 69 |
| Serotype 4 - strain GX0 | 1 | 471 | 90 |
| Serotype 4 - strain HPS | 1 | 523 | 97 |
| Serotype 5 - strain 297 | 1 | 523 | 99 |
| Serotype 5 - strain Nag | 1 | 523 | 98 |
| Serotype 5 - strain SH0 | 1 | 523 | 99 |
| Serotype 9 - strain D74 | 1 | 727 | 70 |
| Serotype 12 - strain ZJ | 1 | 523 | 98 |
| Serotype 13 - strain MN | 1 | 503 | 95 |
| Serotype 15 - strain 84 | 1 | 523 | 99 |

Next to the above, the Mac-1 domain of *H. parasuis* was identified, and herewith disclosed as SEQ ID No:2. The protein according to SEQ ID No:1 is derived from the putative extracellular serine protease of *Haemophilus parasuis* serotype 5, strain SH0165 (Genbank No ACL32961.1), having a length of 780 amino acids. When removing the autotransporter domain (AA's 521 to 780), and performing a HMMR identification (see www.hmmer.org; Robert Finn et al in *Nucleic Acids Research,* 2011 Jul. 1; 39, Web Server issue, W29-W37), the Mac-1 family domain is indicated to start at AA 130 and ending at AA 221.

When comparing the Mac-1 domain of *H. parasuis* with the Mac-1 domain of *Streptococcus suis* there is only a 17% identity (using Blastp), which is an indication that only a small part of the domain is essential for the antibody binding and/or protease activity. Next to this, this is an indication that although the Mac-1 domain is present with 100% identity in various *H. parasuis* serotypes (as indicated here above; notwithstanding that in other strains or serotypes the level of identity is lower), variations of the naturally occurring protein are likely to induce effective antibodies against the natural protein, at least variations within 70% identity level or more.

Example 2

Objective

The objective of this study was to test the efficacy of a subunit vaccine compared to a conventional bacterin vaccine against *H. parasuis* serotype 5 challenge. The subunit vaccine comprised the polypeptide according to SEQ ID No:1, wherein the corresponding DNA was cloned from *H. parasuis* serotype 5, strain SH0165 (Genbank No. ACL32961.1), expressed in an *E. coli* expression vector system (pET22b, with pelB signal sequence and a HIS tag). The bacterin vaccine contained inactivated cells of *Haemophilus parasuis* bacteria of serotype 5.

Study Design

For this study thirty healthy piglets at 4 weeks of age were used. The piglets were allotted to three groups (evenly distributed over the different litters) of 10 piglets each. Group 1 was vaccinated twice intramuscularly at 4 and 6 weeks of age with 2 ml of a vaccine containing the subunit at 75 μg/ml, suspended in an oil in water adjuvant. Group 2 was vaccinated twice intramuscularly with the bacterin vaccine, comprising the inactivated cells suspended in an oil in water adjuvant, and group 3 was left unvaccinated as challenge control. At 8 weeks of age the pigs were challenged intra-tracheally with a virulent culture of *H. parasuis* serotype 5.

During 10 days after challenge the pigs were observed daily for clinical signs of *H. parasuis* infection such as depression, locomotory problems and/or neurological signs and scored using a standard scoring system. Just before each vaccination and challenge, serum blood was collected for antibody determination. At regular times before and after challenge heparin blood was collected for re-isolation of challenge strain. Necropsy was performed on all animals that were culled before the scheduled day of necropsy as well as on all surviving animals.

Results

Before challenge, no abnormalities were observed and no intercurrent death occurred. Average survival time in days, average clinical scores, the number of animals that needed to be euthanized before the end of the study as well as the blood re-isolation results are indicated here below in table 2.

TABLE 2

Results of vaccination - challenge study

| Group | Average survival time (days) | Average clinical score | # euthanised | # blood culture positive |
|---|---|---|---|---|
| Subunit | 7.7 | 27.1 | 3/10 | 3/10 |
| Bacterin | 4.9 | 47.4 | 6/10 | 3/10 |
| Control | 2.0 | 71.0 | 9/10 | 6/10 |

CONCLUSION

The results indicate that the recombinant subunit vaccine induced very good protection against *H. parasuis* challenge. Protection induced was superior to that induced by a bacterin vaccine.

The invention claimed is:

1. A method to protect a pig against an infection with *Haemophilus parasuis* comprising administering to the pig a vaccine that comprises a *Haemophilus parasuis* serine protease antigen, wherein the antigen consists of the amino acid sequence of SEQ ID NO: 2 or the amino acid sequence of SEQ ID NO: 1 or the amino acid sequence having at least 69% sequence identity to amino acid residues 1 to 520 of SEQ ID NO: 1 and also comprising the amino acid sequence of SEQ ID NO: 2.

2. The method of claim 1, wherein the amino acid sequence of the antigen has at least 90% sequence identity with the amino acid sequence of SEQ ID NO: 1.

3. The method of claim 2, wherein the amino acid sequence of the antigen that at least 95% sequence identity with the amino acid sequence of SEQ ID NO: 1.

4. The method of claim 1, wherein said administering the vaccine to the pig protects against an increased risk of mortality due to the infection with *Haemophilus parasuis*.

5. The method of claim 1, wherein said administering the vaccine to the pig protects the pig against one or more clinical signs due to the infection with *Haemophilus parasuis*.

6. An immunogenic composition comprising a serine protease antigen wherein the antigen consists of the amino acid sequence of SEQ ID NO: 2 and an adjuvant.

7. The immunogenic composition of claim 6 for use in a method to induce an immune response in a pig, wherein the immune response is a T- or B-cell immune response.

* * * * *

SEQUENCE LISTING

```
<160> NUMBER OF SEQ ID NOS: 2

<210> SEQ ID NO 1
<211> LENGTH: 520
<212> TYPE: PRT
<213> ORGANISM: Haemophilus parasuis

<400> SEQUENCE: 1

Met Lys Pro Tyr Leu Ser Lys Ile Val Ile Ala Thr Leu Phe Ser Ser
1               5                   10                  15

Ser Val Gln Val Val Glu Ala Gln Thr Tyr Trp Ala Ser Gly Val Asn
            20                  25                  30

Gln Asn Ser Gly Trp Thr Ala Asp Leu Gln Tyr Pro Asn Gln Cys Trp
        35                  40                  45

Gly Ala Val Ala Gly Asn Thr Leu Gly Trp Trp Lys Ser Arg Val Lys
    50                  55                  60

Ala Gln Val Glu Phe Asn Glu Asp Thr Pro Lys Asp Ser Lys Ala Ile
65                  70                  75                  80

Ser Gly Trp Ile Tyr Lys Thr Tyr Pro His Ile Gln Gly Gly Leu Gln
                85                  90                  95

Pro Tyr Arg Gly Met Glu Tyr Phe Phe Ser Arg Phe Ala Ser Gly Val
            100                 105                 110

Lys Leu Tyr Glu Glu His Asn Lys Lys Thr Tyr Tyr Glu Ser Glu Arg
        115                 120                 125

Gly Pro Thr Lys Ile Ser Gly Gly Pro Phe Trp Thr Glu Arg Tyr Asp
    130                 135                 140

Ser Asp Ala Lys Leu Val Thr Lys Ser Leu Ile Asp Asn Phe Lys Thr
145                 150                 155                 160

Gly Asn Val Val Ala Ala Leu Thr Ser Gln His His Thr Val Thr Leu
                165                 170                 175

Trp Gly Ile Glu Val Asp Gly Asp Gly Lys Ile Lys Lys Gly Trp Ile
            180                 185                 190

Ser Asp Ser Val Lys Asp Lys Ala Gly Asn Leu Lys Met Val Glu Val
        195                 200                 205

Val Gly Asn Tyr Ala Lys Asp Asn Lys Gly Asn Asp Ile Phe Arg Phe
    210                 215                 220

Leu Tyr Ser Tyr Ala Val Asp Gly Gly Arg Met Tyr Val Thr Asp Leu
225                 230                 235                 240
```

```
Tyr Asp Ile Tyr Ser Ile Thr Tyr Leu Ser Ile Asp Glu Ala Arg Asn
                245                 250                 255

Asn Gly Thr Tyr Lys Asp Thr Ser Asn Arg Glu Asp Cys Arg Leu Ser
            260                 265                 270

Leu Ala Pro Gly Val Ser Glu Ser Phe Cys Ser Ile Asn Ser Thr Ala
        275                 280                 285

Thr Asn Thr Thr Lys Val Glu Asn Val Ser Thr Thr Ser Asn Asn Ser
    290                 295                 300

Thr Asn Leu Pro Thr Lys Val Glu Asn Ser Gly His Ser Asn Gln Ala
305                 310                 315                 320

Ile Asn Ala Ala Ser Ala Ser Asp Asp Thr Val Ser Ser Ala Ser Glu
                325                 330                 335

Asn Asn Asp Ser Val Asn Thr Pro Glu Asn Ile Glu Asn Ser Asn Gly
            340                 345                 350

Val Asp Ile Gly Asn Asn Ser Thr Val Ser Ser Ala Asn Val Glu Asn
        355                 360                 365

Ser Ser Asn Glu Val Ser Val Ile Asn Thr Pro Asn Thr Ser Ser Leu
    370                 375                 380

Pro Asn Asp Gln Gly Thr Lys Lys Ile Ile Val Asp Ser Ser Glu Ser
385                 390                 395                 400

Asn Ala Lys Asp Pro Ile Ile Ser Lys Ala Thr Glu Ser Leu Thr Lys
                405                 410                 415

Glu Ile Asn Ser Tyr Pro Glu Leu Ser Phe Ile Thr Lys Asn Met Gly
            420                 425                 430

Asp Val Thr Phe Tyr Ile Val Gln Lys Asp Gly Val Asp Ile Thr Leu
        435                 440                 445

Ile Asn Pro Lys Thr Glu Gln Ser Leu Val Ser Asn Lys Gly Leu Val
    450                 455                 460

Ile Tyr Asp Phe Lys Gln Gly Gln Asn Gly Asn Ile His Ile Thr Lys
465                 470                 475                 480

Ser Pro Asn Gln Ala Ala Ile Lys Glu Ala Asn Glu Val Thr Ser Leu
                485                 490                 495

His Thr Asp Leu Asn His Val Glu Met Asn Asn Leu Asn Lys Arg Met
            500                 505                 510

Gly Glu Leu Arg Gly Ile Asp Ala
        515                 520


<210> SEQ ID NO 2
<211> LENGTH: 92
<212> TYPE: PRT
<213> ORGANISM: Haemophilus parasuis

<400> SEQUENCE: 2

Pro Thr Lys Ile Ser Gly Gly Pro Phe Trp Thr Glu Arg Tyr Asp Ser
1               5                   10                  15

Asp Ala Lys Leu Val Thr Lys Ser Leu Ile Asp Asn Phe Lys Thr Gly
            20                  25                  30

Asn Val Val Ala Ala Leu Thr Ser Gln His His Thr Val Thr Leu Trp
        35                  40                  45

Gly Ile Glu Val Asp Gly Asp Gly Lys Ile Lys Lys Gly Trp Ile Ser
    50                  55                  60
```

-continued

```
Asp Ser Val Lys Asp Lys Ala Gly Asn Leu Lys Met Val Glu Val Val
65                  70                  75                  80

Gly Asn Tyr Ala Lys Asp Asn Lys Gly Asn Asp Ile
                85                  90
```